United States Patent [19]

Ohashi et al.

[11] Patent Number: 5,159,089
[45] Date of Patent: Oct. 27, 1992

[54] SELECTIVE PRODUCTION OF THREO-EPOXY COMPOUNDS

[75] Inventors: Naohito Ohashi, Takatsuki; Koji Fujimoto, Ibaraki; Yoshihiro Tanaka, Ikeda, all of Japan

[73] Assignee: Sumitomo Pharmaceuticals Company, Limited, Osaka, Japan

[21] Appl. No.: 572,122

[22] Filed: Aug. 24, 1990

[30] Foreign Application Priority Data

Aug. 28, 1989 [JP] Japan ................................. 1-222454

[51] Int. Cl.$^5$ .......................................... C07D 301/02
[52] U.S. Cl. ....................................... 549/519; 549/556
[58] Field of Search ............................. 549/519, 556

[56] References Cited

U.S. PATENT DOCUMENTS

| | | | |
|---|---|---|---|
| 4,925,961 | 5/1990 | Ikeda et al. | 549/521 |
| 4,988,829 | 6/1991 | Fiedler et al. | 549/519 |
| 4,992,565 | 2/1991 | Mohrmann et al. | 549/519 |

FOREIGN PATENT DOCUMENTS

| | | | |
|---|---|---|---|
| 178533 | 4/1986 | European Pat. Off. | 549/519 |
| 0140154 | 2/1989 | European Pat. Off. | |

OTHER PUBLICATIONS

G. Gokel et al., *J. Chem. Ed.*, "Phase-transfer Catalysis," 55(6), pp. 350-354 (1978).
W. Weber et al., *J. Chem. Ed.*, "Phase-transfer Catalysis" 55(7), pp. 429-433 (1978).
F. Carey, et al., "Advanced Organic Chemistry," 2nd ed., Part B, pp. 78-83, Plenum Press, New York (1983).
E. Corey, et al., *J. Am. Chem. Soc.*, "Dimethyloxosulfonium Methylide (CCH$_3$)$_2$SOCH$_2$) ... " 87(6), pp. 1353-1364 (1965).
C. J. M. Stirling and S. Patai: "The Chemistry of the Sulphonium Group," Chap. 12, pp. 313, 355-385, by A. C. Knipe.
Gololobov et al., Tetrahedron, vol. 43, No. 12, 1987, London, pp. 2609-2651.
Summary of the 8th Medicinal Chemistry Symposium, 1986, Nov. 27-28, Osaka, pp. 9-12 with English translation thereof.
Fray et al., Journal of the Chem. Society Perkin Trans. I., 1983, London, pp. 395-401.

*Primary Examiner*—Richard L. Raymond
*Assistant Examiner*—Mark W. Russell
*Attorney, Agent, or Firm*—Birch, Stewart, Kolasch and Birch

[57] ABSTRACT

A process for selective production of a threo-epoxy compound of the formula:

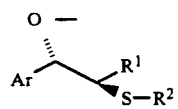

wherein Ar is a substituted or unsubstituted phenyl group and $R^1$ and $R^2$ are each a lower alkyl group, which comprises reacting a ketone compound of the formula:

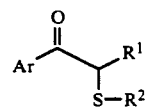

wherein Ar, $R^1$ and $R^2$ are each as defined above with a sulfur methylide of the formula:

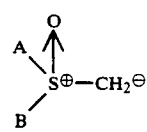

wherein A is a lower alkyl group or a substituted or unsubstituted phenyl group and B is a lower alkyl group, a substituted or unsubstituted phenyl group or a di(lower)-alkylamino group in an aqueous organic solvent.

25 Claims, No Drawings

SELECTIVE PRODUCTION OF THREO-EPOXY COMPOUNDS

The present invention relates to selective production of threo-epoxy compounds. More specifically, it relates to selective production of the threo isomers of epoxy compounds of the formula:

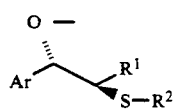
(III)

wherein Ar is a substituted or unsubstituted phenyl group and $R^1$ and $R^2$ are each a lower alkyl group.

It is known that the benzyl alcohol derivatives of the formula:

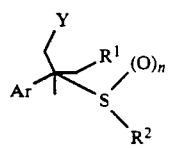
(IV)

wherein Ar, $R^1$ and $R^2$ are each as defined above, Y is a triazole or imidazole group and n is an integer of 0, 1 or 2 are useful as antifungal agents (JP-A-61-85369). Since the benzyl alcohol derivatives (IV) have two asymmetric carbon atoms, there can exist two kinds of stereo isomers, i.e., threo isomers and erythro isomers. Of these two kinds of isomers, the threo isomers generally exhibit higher antifungal activity than the erythro isomers. Because of this, the predominant production of the threo isomers is desired.

Production of the benzyl alcohol derivatives (IV) can be accomplished, for instance, through the reaction of a corresponding ketone compound of the formula:

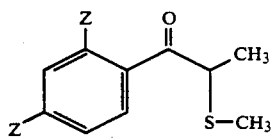
(V)

wherein Z is a fluorine atom or a chlorine atom with sulfur methylide in a non-aqueous solvent system to give an epoxy compound of the formula:

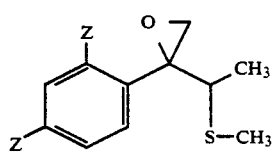
(VI)

wherein Z is as defined above. The above reaction can give the erythro isomer of the epoxy compound (VI) stereo-specifically via the choice of suitable conditions, but the threo isomer is obtainable only in its mixture with the erythro isomer in a molar ratio of 1:1 at the most. The predominant production of the threo isomer is thus not possible (Summary of Speeches at the 8th Medicinal Chemistry Symposium, Nov. 27-28, 1986, Osaka, page 9). Accordingly, the efficient production of the threo isomer of the benzyl alcohol derivative (IV) through the epoxy compound (VI) as produced by the above reaction is difficult.

In view of the reason as set forth above, the threo isomer of the benzyl alcohol derivative (IV) is practically produced, for instance, according to the following scheme:

Scheme A

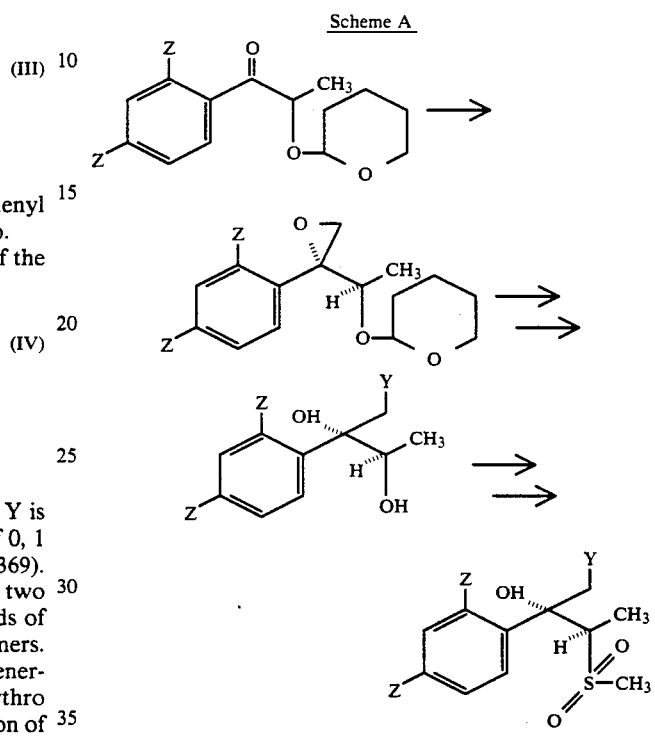

wherein Y and Z are each as defined above. However, the process according to Scheme A requires several steps for introduction of a sulfur atom into the molecule so that the total synthesis of the threo isomer of the, benzyl alcohol derivative (IV) is quite lengthy and can not be accomplished economically.

In summary, the use of the ketone compound (V) having a sulfur atom therein as the starting material affords the objective benzyl alcohol derivative (IV) in fewer steps, but the selectivity of the threo isomer is low. On the other hand, the adoption of the process as shown in Scheme A gives the threo isomer predominantly, but requires a lengthy series of steps.

An object of the present invention is to provide an industrially advantageous process for production of the threo isomer of the benzyl alcohol derivative (IV) with high selectivity through fewer steps.

In order to attain said object, an extensive study has been made, and as a result, it has been found that the epoxidation of a ketone compound of the formula:

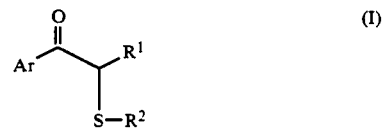
(I)

wherein Ar, $R^1$ and $R^2$ are each as defined above under a certain specific condition affords predominantly the threo isomer of the epoxy compound (III), i.e. the threo-epoxy compound of the formula:

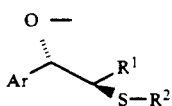

(III)

wherein Ar, $R^1$ and $R^2$ are each as defined above.

Namely, the epoxidation of the ketone compound (I) with a sulfur methylide of the formula:

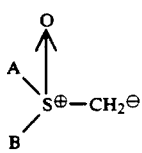

(II)

wherein A is a lower alkyl group or a substituted or unsubstituted phenyl group and B is a lower alkyl group, a substituted or unsubstituted phenyl group or a di(lower)alkylamino group gives the epoxy compound usually as a mixture of two kinds of stereo-isomers, of which one is the threo isomer (III) and the other is the erythro isomer of the formula:

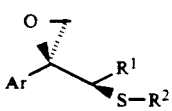

(III')

wherein Ar, $R^1$ and $R^2$ are each as defined above. When the epoxidation is effected in an aqueous organic solvent as the reaction medium, the reaction proceeds stereospecifically to give the product comprising the threo isomer (III) predominantly, e.g., with a threo isomer/erythro isomer ratio of 4/1 or more. Such remarkable enhancement of the threo isomer/erythro isomer ratio by the use of a certain specific reaction medium in the epoxidation is of a surprising nature, and is not obvious from any prior art.

The threo isomer (III) thus produced can be reacted with a triazole or an imidazole, optionally followed by oxidation of the sulfur atom to give the threo isomer of the benzyl alcohol derivative (IV) (Summary of Speeches at the 8th Medicinal Chemistry Symposium, 1986, Nov. 27-28, Osaka, page 9).

The process of this invention comprises reacting the ketone compound (I) with the sulfur methylide (II) in an aqueous organic solvent to give the threo isomer of the epoxy compound (III) predominantly.

In this specification, the term "lower" used in connection with any atomic group is intended to mean a group having not more than 8 carbon atoms, preferably not more than 4 carbon atoms (e.g., methyl, ethyl, propyl, butyl). The term "substituted phenyl" group is intended to mean a phenyl group bearing thereon one or more, preferably not more than three, substituents chosen from halogen (e.g., fluorine, chlorine, bromine), lower alkyl (e.g., methyl, ethyl, n-propyl, isopropyl, n-butyl, t-butyl, isobutyl, s-butyl), lower alkoxy (e.g., methoxy, ethoxy), lower alkylenedioxy (e.g., methylenedioxy, ethylenedioxy), nitro, hydroxyl, etc. Specific examples of the substituted phenyl group are 2,4-difluorophenyl, 2,4-dichlorophenyl, p-chlorophenyl, p-tolyl, 2-mesityl, etc. The symbol $X^\ominus$ represents an atomic or molecular ion capable of serving as a counter anion to a sulfur cation. Examples of such anions are $Cl^\ominus$, $Br^\ominus$, $I^\ominus$, $BF_4^\ominus$, $ClO_4^\ominus$, $HO^\ominus$, etc.

The ketone compound (I) is obtainable, for instance, according to the method as described in Summary of Speeches at the 8th Medicinal Chemistry Symposium as recited above. Specific examples of the ketone compound (I) are 2-methylthio-2',4'-difluoropropiophenone, 2-methylthio-2',4'-dichloropropiophenone, etc.

The sulfur methylide (II) can be prepared by treating an oxosulfonium salt of the formula:

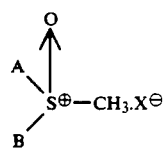

(VII)

wherein $X^-$ is an atomic or molecular ion capable of serving as a counter anion to a sulfur cation and A and B are each as defined above with a base.

Said oxosulfonium salt is obtainable, for instance, by the method as described in M. Trost: Sulfur Ylides (1975), Academic Press. Specific examples of the oxosulfonium salt (VII) are trimethyloxosulfonium iodide, trimethyloxosulfonium bromide, trimethyloxosulfonium chloride, dimethylamino-phenyl-methyloxosulfonium fluoroborate, dimethylamino-p-tolyl-methyloxosulfonium fluoroborate, dimethylamino-dimethyloxosulfonium fluoroborate, dimethylamino-2-mesityl-methyloxosulfonium fluoroborate, etc.

The process of the invention may be carried out by treating the oxosulfoninium salt (VII) with a base to prepare the sulfur methylide (II) and then reacting the thus prepared sulfur methylide (II) onto the ketone compound (I) in an aqueous organic solvent. Alternatively, it may be carried out by treatment of the ketone compound (I) with the oxosulfonium salt (VII) in an aqueous organic solvent in the presence of a base so that the sulfur methylide (II) is once formed in the reaction system and then reacted with the ketone compound (I). The latter is advantageous in the simplicity of operation.

As explained above, the process according to the invention is usually performed by treatment of the ketone compound (I) with the oxosulfonium salt (VII) in an aqueous organic solvent containing a base, normally with stirring to give the threo isomer of the epoxy isomer (III) stereoselectively. In the above treatment, the oxosulfonium salt (VII) is once converted into the sulfur methylide (II), which is then reacted with the ketone compound (I).

The amount of the oxosulfonium salt (VII) may be one mole or more to one mole of the ketone compound (I), and normally the use of the former in a 1 to 2 molar amount to one mole of the latter is preferred from the viewpoints of the yield and the by-products.

The reaction is carried out under basic conditions, usually at a pH of not less than about 10, preferably of not less than about 14. No upper limit is present on the pH. In order to make the reaction system basic, an alkaline reagent such as an inorganic base is preferably employed. Specific examples of the inorganic base are strongly alkaline substances such as hydroxides or carbonates of alkali metals or alkaline earth metals, among which are preferred sodium hydroxide, potassium hydroxide, etc. The concentration of these strongly alkaline substances is not limitative but may be from about 10 % by weight to saturation. The alkaline reagent may be used normally in an equimolar amount or more to the oxosulfonium salt (VII), and the use of five moles or more of the former to one mole of the latter is preferred.

The reaction medium comprises an aqueous organic solvent, i.e., a mixture of water and at least one organic solvent. As the organic solvent, there may be used lower alcohols (e.g., ethylene glycol, isopropyl alcohol, t-butyl alcohol, sec-butyl alcohol), ethers (e.g., diethyl ether, dioxane, tetrahydrofuran), aromatic or halogenated aromatic hydrocarbons (e.g., toluene, xylene, benzene, chlorobenzene, dichlorobenzene), halogenated aliphatic hydrocarbons (e.g., methylene chloride, 1,2-dichloroethane, hydrocarbons (e.g., n-hexane, cyclohexane), etc. These organic solvents may be used solely or in combination at an optional mixing ratio. For attaining a higher threo isomer/erythro isomer ratio, the use of halogenated aliphatic hydrocarbons (e.g., methylene chloride, dichloroethane) is preferred. On the other hand, the use of aromatic or halogenated aromatic hydrocarbons (e.g., toluene, chlorobenzene) or their mixtures with lower alcohols (e.g.,t-butyl alcohol) is favorable from the viewpoint of easy operation. The organic solvent is usually employed in an amount of about 1 to 100 fold by weight to the ketone compound (I), and the use in an amount of about 5 to 50 fold is preferred for easy operation.

The proportion of the water and the organic solvent in the reaction medium is normally from about 100:1 to 1:100, preferably from about 10:1 to 1:10, for formation of the two-phase solvent system.

The reaction can proceed sufficiently at room temperature, but heating up to the boiling temperature may be applied when desired. If necessary, a phase transfer catalyst may be used for acceleration of the reaction or enhancement of the threo isomer/erythro isomer ratio. Examples of the phase transfer catalyst are tetra-n-butylammonium iodide, tetra-n-butylammonium sulfate, hexadecylpyridinium chloride, dodecyltrimethylammonium bromide, benzyltrimethylammonium bromide, etc. Further, the reaction may be conducted in the atmosphere of an inert gas (e.g., nitrogen, helium, argon).

When the reaction is carried out by treatment of the ketone compound (I) with the, sulfur methylide (II) as preliminarily prepared, substantially the same reaction conditions as adopted in the reaction by treatment of the ketone compound (I) with the oxosulfonium salt (VII) may be employed.

As mentioned above, the sulfur methylide (II) can be preliminarily prepared by treating the oxosulfonium salt (VII) with a base in a non-aqueous solvent, normally at a temperature of about 0° C. to room temperature. If necessary, the treatment is performed while heating. As the non-aqueous solvent, there may be used any one appropriately chosen from ethers, aromatic or halogenated aromatic hydrocarbons, aliphatic hydrocarbons, etc. Further, any base chosen from n-butyl lithium, sodium hydride, sodium alkoxide, etc. may be used. The sulfur methylide (II) thus obtained may be, without isolation, used for the reaction with the ketone compound (I) in the presence of an aqueous medium such as water, an aqueous strongly alkaline solution or a saturated sodium chloride solution to give the epoxy compound (III).

Separation and purification of the produced epoxy compound (III) from the reaction mixture may be conducted by a per se conventional procedure. When, for instance, the organic solvent is water-immisicible, the organic layer containing the epoxy compound (III) is separated from the reaction mixture, and the epoxy compound (III) is recovered from the organic layer. When the organic solvent is water-miscible, the epoxy compound (III) may be extracted with a water-immiscible organic solvent.

According to the present invention, the threo isomer of the epoxy compound (III) can be produced stereoselectively, and the threo isomer of the benzyl alcohol derivative (IV) can be thus obtainable efficiently therefrom.

Practical and presently preferred embodiments of the invention are illustratively shown in the following examples.

EXAMPLE 1

To trimethyloxosulfonium iodide (259.5 g), there were added 2-methylthio-2',4'-difluoropropiophenone (165 g) and dichloroethane (1702 g), and 48 % aqueous sodium hydroxide solution (4717 g) was added thereto under a nitrogen stream. The resultant mixture was heated to an inner temperature of 70° C. and stirred for 6 hours. Upon confirmation of the disappearance of 2-methylthio-2',4'-difluoropropiophenone by high performance liquid chromatography (HPLC), the reaction mixture was combined with water (1700 g). The aqueous layer was separated from the dichloroethane layer and extracted with dichloroethane (425 g). The dichloroethane layers were combined together, washed with water (1700 g) twice and concentrated to dryness to give 191.5 g of threo-2-(2,4-difluorophenyl)-2-(1-methylthioethyl)oxirane as an oil. The HPLC analysis on this product showed that the threo isomer/ethythro isomer ratio was about 6/1 and the content of the threo isomer was 61.9%.

EXAMPLE 2

To 2-methylthio-2',4'-difluoropropiophenone (40 g), there were added toluene (206 g), tert-butanol (51.6 g), trimethyloxosulfonium iodide (46.2 g) and 48 % aqueous sodium hydroxide solution (397 g) under a nitrogen stream. The resultant mixture was heated to an inner temperature of 80° C. and stirred for 3 hours. Upon confirmation of the disappearance of 2-methylthio-2',4'-difluoropropiophenone by HPLC, the toluene layer was separated from the aqueous layer at an inner temperature of 60° to 70° C. The toluene layer was washed with water (400 g) twice and concentrated to dryness to give 47.1 g of threo-2-(2,4-difluorophenyl)-2-(1-methylthioethyl)oxirane as an oil. The HPLC analysis on this product showed that the threo isomer/ethythro isomer ratio was about 5/1 and the content of the threo isomer was 65.6 %.

EXAMPLE 3

To 2-methylthio-2',4'-difluoropropiophenone (0.43 g), there were added dichloromethane (4.5 g) and trimethyloxosulfonium chloride (0.38 g) under a nitrogen stream, and 50 % aqueous sodium hydroxide solution (8.0 g) was added thereto at room temperature. The resultant mixture was kept at the same temperature while stirring for 2 hours. Upon confirmation of the disappearance of 2-methylthio-2',4'-difluoropropiophenone by HPLC, the reaction mixture was combined with water (50 ml) and dichloromethane (50 ml) for extraction. The aqueous layer was separated from the dichloromethane layer and extracted with dichloromethane (30 ml). The dichloromethane extract was combined with the dichloromethane layer and washed with water (100 ml) twice. The dichloromethane layer was dried over magnesium sulfate and concentrated to dryness to give 0.45 g of threo-2-(2,4-difluorophenyl)-2-(1-methylthioethyl)oxirane as an oil. The HPLC analysis on this product showed that the threo isomer/ethythro isomer ratio was about 7/1.

EXAMPLE 4

To 2-methylthio-2',4'-difluoropropiophenone (0.43 g), there were added an organic solvent (4.3 g) as shown in the table below, trimethyloxosulfonium iodide (0.66 g) and 48% aqueous sodium hydroxide solution (11.9 g), and the resultant mixture was allowed to react at 70° C. under a nitrogen stream for a designated period of time to give threo-2-(2,4-difluorophenyl)-2-(1-methylthioethyl)oxirane. The results are shown in the table below.

TABLE

| Run No. | Organic solvent | Reaction time (hour) | Threo isomer/ erythro isomer ratio |
|---|---|---|---|
| 1 | Xylene | 13 | 7.0/1 |
| 2 | Chlorobenzene | 7 | 7.4/1 |
| 3 | Toluene | 10 | 7.8/1 |
| 4 | t-Butanol | 1 | 4.3/1 |
| 5 | o-Dichlorobenzene | 6 | 6.5/1 |

EXAMPLE 5

To 2-methylthio-2',4'-difluoropropiophenone (0.43 g), there were added dichloromethane (4.5 g), trimethyloxosulfonium iodide (0.66 g) and tetrabutylammonium iodide (0.37 g), and 50 % sodium hydroxide solution (8.0 g) was added thereto under a nitrogen stream, followed by stirring at room temperature for 24 hours. The HPLC analysis on the reaction mixture containing threo-2-(2,4-difluorophenyl)-2-(1-methylthioethyl)oxirane showed that the threo isomer/ethythro isomer ratio was about 6/1.

EXAMPLE 6

To 2-methylthio-2',4'-difluoropropiophenone (0.43 g), there were added 1,2-dichloroethane (4.3 g) and trimethyloxosulfonium iodide (0.66 g), and 48 % potassium hydroxide solution (15.0 g) was added thereto under a nitrogen stream. The inner temperature of the resultant mixture was raised to 70° C, followed by stirring for 4 hours. The HPLC analysis on the reaction mixture containing threo-2-(2,4-difluorophenyl)-2-(1-methylthioethyl)oxirane showed that the threo isomer/erythro isomer ratio was about 6/1.

EXAMPLE 7

According to the method reported by E. J. Corey et al. (J.Am.Chem.Soc., 87, 1353 (1965)), chlorine gas was blown into an aqueous solution of trimethyloxosulfonium iodide to prepare an aqueous solution of trimethyloxosulfonium chloride. To the thus prepared trimethyloxosulfonium chloride solution (about 0.4 mol/l ) (6.54 g), there were added 2-methylthio-2',4'-difluorophenylpropiophenone (0.43 g), dichloromethane (4.3 g) and sodium hydroxide (6.0 g), and the resultant mixture was stirred at room temperature overnight. Upon confirmation of the disappearance of 2-methylthio-2' 4'-difluorophenylpropiophenone by HPLC, the reaction mixture was treated in the same manner as in Example 3 to give 0.37 g of threo-2-(2,4-difluorophenyl)-2-(1-methylthioethyl)oxirane as an oil. The HPLC analysis on this product showed that the threo isomer/ethythro isomer ratio is about 8/1 and the content of the threo isomer was 75.8 %.

REFERENCE EXAMPLE 1

Production of threo-2-(2,4-difluorophenyl)-3-methylthio-1-(1H-1,2,4-triazol-1-yl)butan-2-ol To threo-2-(2,4-difluorophenyl)-2-(1-methylthioethyl)oxirane (threo isomer/erythro isomer =5/1 by HPLC; content, 63.6 %) (31.4 g) obtained as in Example 2, there were added dimethylsulfoxide (110 g), 1H-1,2,4-triazole (9.0 g) and sodium hydroxide (3.5 g), and the resultant mixture was heated to 80° C. (inner temperature), followed by stirring for 3 hours. Upon confirmation of the disappearance of threo-2-(2,4-difluorophenyl)-2-(1-methylthioethyl)oxirane by HPLC, the reaction mixture was cooled to room temperature and combined with toluene and dilute hydrochloric acid, followed by extraction. The aqueous layer was separated from the toluene layer and extracted with toluene. The toluene layers were combined together, washed with dilute hydrochloric acid and water in order and concentrated. After addition of heptane, the precipitated crystals were collected by filtration to give 17.0 g of threo-2-(2,4-difluorophenyl)-3-methylthio-1-(1H-1,2,4-triazol-1-yl)butan-2-ol as crystals. The HPLC analysis on this product showed that the threo isomer/erythro isomer ratio was more than 100/1 and the content of the threo isomer was 99.2 %.

M.P., 122–123° C.

Elementary analysis for $C_{13}H_{15}OF_2N_3S$ (%):

Calcd.: C, 52.16; H, 5.05; N, 14.04; S, 10.71.
Found: C, 52.13; H, 5.07; N, 13.87; S, 10.8.

REFERENCE EXAMPLE 2

Production of threo-2-(2,4-difluorophenyl)-3-methylsulfonyl-1-(1H-1,2,4-triazol-1-yl)butan-2-ol To threo-2-(2,4-difluorophenyl)-3-methylthio-1-(1H-1,2,4-triazol-1-yl)butan-2-ol (content, 84.4 %) (25.0 g) obtained as in Reference Example 1, there were added methanol (125 g), sodium tungstate (55 mg) and conc. hydrochloric acid (13.0 g), and the resultant mixture was stirred at room temperature while dropwise addition of 35 % aqueous hydrogen peroxide solution (19.5 g). The reaction mixture was heated to 60° C. and stirred for 3 hours. Upon confirmation of the disappearance of threo-2-(2,4-difluorophenyl)-3-methylthio-1-(1H-1,2,4-triazol-1-yl)butan-2-ol by HPLC, the reaction mixture was cooled to room temperature, followed by addition of 5 % aqueous sodium thiosulfate solution to reduce excess hydrogen peroxide. The resulting mixture was neutralized with 10 % aqueous sodium hydroxide solution, and the precipitated crystals were collected by filtration to give 22.6 g of threo-2-(2,4-difluorophenyl)-methylsulfonyl-1-(1H-1,2,4-triazol-1-yl)butan-2-ol. The HPLC analysis on this product showed that no erythoro isomer was contained therein, and the content of the threo isomer was 99.0 %.

M.P., 207–209° C.

The crystals thus obtained were recrystallized from methanol using active carbon to give purified threo-2-(2,4-difluorophenyl)-3-methylsulfonyl-1-(1H-1,2,4-triazol-1-yl)butan-2-ol. The content of the threo isomer was 99.9%.

M.P., 209–210° C.

Elementary analysis for $C_{13}H_{15}OF_2N_3S$ (%)
Calcd.: C, 47.13; H, 4.56; N, 12.68; S, 9.68.
Found: C, 46.93; H, 4.53; N, 12.56; S, 9.6.

What is claimed is:

1. A process for selective production of a threo-epoxy compound of the formula:

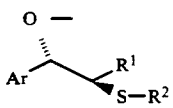

wherein Ar is a substituted or unsubstituted phenyl group and $R^1$ and $R^2$ are each a lower alkyl group, which comprises reacting a ketone compound of the formula:

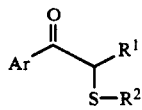

wherein Ar, $R^1$ and $R^2$ are each as defined above with a sulfur methylide of the formula:

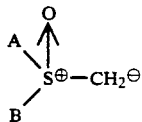

wherein A is a lower alkyl group or a substituted or unsubstituted phenyl group and B is a lower alkyl group, a substituted or unsubstituted phenyl group or a di(lower)-alkylamino group in an aqueous organic solvent, wherein said organic solvent is at least one selected from the group consisting of a lower alcohol selected from the group consisting of ethylene glycol, isopropyl alcohol, t-butyl alcohol, and sec-butyl alcohol; an ether selected from the group consisting of diethyl ether, dioxane, and tetrahydrofuran; an aromatic or halogenated aromatic hydrocarbon selected from the group consisting of toluene, xylene, benzene, chlorobenzene, and dichlorobenezene; a halogenated aliphatic hydrocarbon selected from the group consisting of methylene chloride and 1,2-dichloroethane; and a hydrocarbon selected from the group consisting of n-hexane and cyclohexane.

2. The process according to claim 1, wherein $R_1$ and $R_2$ are each a $C_1$-$C_4$ alkyl group and Ar is a halogenated phenyl group.

3. The process according to claim 1, wherein $R_1$ and $R_2$ are each a methyl group and Ar is a 2,4-difluorophenyl group.

4. The process according to claim 1, wherein A and B are each a methyl group.

5. The process according to claim 1, wherein said organic solvent is one selected from halogenated aliphatic hydrocarbons.

6. The process according to claim 1, wherein said organic solvent is one selected from aromatic hydrocarbons.

7. The process according to claim 1, wherein said organic solvent is a mixture of aromatic hydrocarbons and t-butyl alcohol.

8. The process according to claim 1, wherein said aqueous organic solvent is an aqueous inorganic alkaline solution and an organic solvent.

9. The process according to claim 1, wherein the water/organic solvent ratio of said aqueous organic solvent is from 10/1 to 1/10.

10. The process according to claim 1, wherein the water/organic solvent ratio of said aqueous organic solvent is from 3/1 to 1/3.

11. The process according to claim 1, wherein said substituted phenyl group is selected from the group consisting of 2,4-difluorophenyl, 2,4-dichlorophenyl, p-chlorophenyl, p-tolyl, and 2-mesityl.

12. The process according to claim 1, wherein said ketone is selected from the group consisting of 2-methylthio-2', 4'-difluoropropiophenone and 2-methylthio-2'-4'-dichloropropiophenone.

13. The process according to claim 1, wherein the pH of the reaction medium is basic.

14. The process according to claim 8, wherein the concentration of the alkaline substance in said alkaline solution is from about 10% by weight to saturation.

15. The process according to claim 1, wherein said organic solvent is selected from the group consisting of a lower alcohol, an ether, an aromatic hydrocarbon, a halogenated aromatic hydrocarbon, a halogenated aliphatic hydrocarbon, and a hydrocarbon.

16. The process according to claim 5, wherein said halogenated aliphatic hydrocarbon is selected from the group consisting of methylene chloride and dichloroethane.

17. The process according to claim 15, wherein said aromatic or halogenated aromatic hydrocarbon is selected from the group consisting of toluene and chlorobenzene.

18. The process according to claim 1, wherein said organic solvent is an aromatic or halogenated aromatic hydrocarbon, or a mixture thereof, with a lower alcohol.

19. The process according to claim 18, wherein said lower alcohol is t-butyl alcohol.

20. The process according to claim 1, wherein said organic solvent is present in an amount of from about 1 to 100-fold by weight of said ketone compound.

21. The process according to claim 1, wherein said organic solvent is present in an amount of from about 5 to 50-fold by weight of said ketone compound.

22. The process according to claim 1, wherein said process is conducted by heating to boiling.

23. The process according to claim 1, further comprising the use of a phase transfer catalyst.

24. The process according to claim 22, wherein said phase transfer catalyst is selected from the group consisting of tetra-n-butylammonium iodide, tetra-n-butylammonium sulfate, hexadecylpyridinium chloride, dodecyltrimethylammonium bromide, and benzyltrimethylammonium bromide.

25. The process according to claim 1, wherein said process is conducted in an atmosphere of an inert gas.

* * * * *

UNITED STATES PATENT AND TRADEMARK OFFICE
CERTIFICATE OF CORRECTION

PATENT NO. : 5,159,089

DATED : October 27, 1992

INVENTOR(S) : N. Ohashi et al.

It is certified that error appears in the above-identified patent and that said Letters Patent is hereby corrected as shown below:

Replace the first appearing chemical formula in the "Abstract" with:

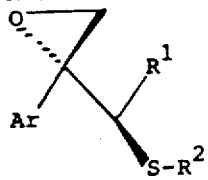

Replace chemical formula (III) at (a) column 1, line 10, (b) at column 3, line 1, and (c) at column 9, line 10 with:

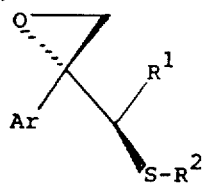

Replace chemical formula (IV) at column 1, line 20 with:

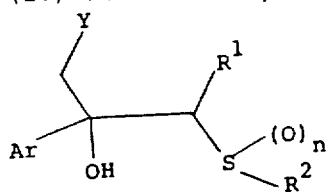

Signed and Sealed this

Sixteenth Day of November, 1993

Attest:

BRUCE LEHMAN

Attesting Officer

Commissioner of Patents and Trademarks